US008431383B2

(12) United States Patent
Xu et al.

(10) Patent No.: US 8,431,383 B2
(45) Date of Patent: Apr. 30, 2013

(54) MUTAGENIZED STRAIN OF *GLAREA LOZOYENSIS* AND A METHOD OF PREPARING A COMPOUND FROM THE MUTAGENIZED STRAIN

(75) Inventors: Jing Xu, Shanghai (CN); Yi Chen, Shanghai (CN); Xiaoming Ji, Shanghai (CN); Xiaoliang Gao, Shanghai (CN); Shidong Liu, Shanghai (CN); Zhaoli Zhang, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 13/497,927

(22) PCT Filed: Sep. 28, 2009

(86) PCT No.: PCT/CN2009/074271

§ 371 (c)(1), (2), (4) Date: Mar. 23, 2012

(87) PCT Pub. No.: WO2011/035492

PCT Pub. Date: Mar. 31, 2011

(65) Prior Publication Data

US 2012/0258498 A1 Oct. 11, 2012

(30) Foreign Application Priority Data

Sep. 24, 2009 (CN) .......................... 2009 1 0196286

(51) Int. Cl.
*C12N 1/20* (2006.01)
*C07K 7/56* (2006.01)

(52) U.S. Cl.
USPC ........................ 435/252.4; 435/70.1; 435/119

(58) Field of Classification Search ........................ None
See application file for complete search history.

(56) References Cited

FOREIGN PATENT DOCUMENTS

| | | |
|---|---|---|
| CN | 1392246 | 1/2003 |
| CN | 1781938 | 6/2006 |
| CN | 1891813 | 1/2007 |
| WO | 00/08197 | 2/2000 |
| WO | 03/054001 | 7/2003 |

OTHER PUBLICATIONS

Connors et al., Appl. Microbiol. Biotechnol. vol. 54, pp. 814-818 2000.*

Masurekar et. al., Pneumocandins from Zalerion arboricola. II. Modification of product spectrum by mutation and medium manipulation, J Antibiot (Tokyo) 45(12), 1867-1874, 1992.*

Huang, Jinzhu et al., "The progress of antifungal agents research," World Notes on Antibiotics, Dec. 31, 2007, vol. 28, No. 6, p. 246-251.

Jiang, Lizheng et al., "The new progress of echinocandin antifungal agents research," Tianjin Pharmacy, Oct. 31, 2005, vol. 17, No. 5, p. 62-64.

Pfaller, M.A. et al., "In Vitro Susceptibility of Invasive Isolates of Candida spp. To Anidulafungin, Caspofungin, and Micafungin: Six Years of Global Surveillance," J. Clin. Microbiol., Sep. 2008, vol. 46, No. 9, p. 3184-3185.

Vazquez, Jose A. et al., "Anidulafungin: A Novel Echinocandin," Clinical Infectious Diseases, Jul. 15, 2006, vol. 43, p. 215-222.

International Search Report for international application No. PCT/CN2009/074271, dated Jun. 17, 2010 (8 pages).

* cited by examiner

*Primary Examiner* — Irene Marx

(74) *Attorney, Agent, or Firm* — Hamre, Schumann, Mueller & Larson, P.C.

(57) ABSTRACT

High yield antibiotics producing fungus strain, preparation method and use thereof are provided. The fungus strain is a mutant derived from *Glarea lozoyensis*, and deposited in CGMCC with the accession number of CGMCC 2933. The preparation method concludes following steps: (a) mixing the culture media of *Glarea lozoyensis* strain ATCC 20957 with nitrosoguanidine, and obtaining mixture a; (b) mixing lywallzyme with the mixture a, and obtaining protoplasts; (c) regenerating the protoplasts, and obtaining single clones; and (d) culturing the single clones, then obtaining the mutant strain. This fungus strain has stable genetic and producing property, produces little impurities in fermentation, and is suitable to be used in industry.

8 Claims, 1 Drawing Sheet

Starting strain → seed liquid → NTG mutagenesis treatment →removing cell wall by lywallzyme to obtain protoplasts → diluting and plating the protoplasts on dishes → picking single colony and seeding it on the slant → primary screening in shake flasks → selecting high-yielding strain → seeding the strain on the slant → secondary screening in shake flasks → selecting high-yielding strain, verifying in fermentation tank, and performing stability experiment → depositing strain

Fig. 1

| Pneumocandin | Position Affected | $R_1$ | $R_2$ | $R_3$ | $R_4$ | $R_5$ | $R_6$ |
|---|---|---|---|---|---|---|---|
| $B_0$ | | H | OH | OH | OH | $CH_3$ | OH |
| $C_0$ | *trans* 3-Hydroxyproline | OH | H | OH | OH | $CH_3$ | OH |
| $D_0$ | " | OH | OH | OH | OH | $CH_3$ | OH |
| $E_0$ | " | H | H | OH | OH | $CH_3$ | OH |
| $A_0$ | " | $CH_3$ | OH | OH | OH | $CH_3$ | OH |
| $B_5$ | Ornithine | H | OH | OH | H | $CH_3$ | OH |
| $B_6$ | " | H | OH | H | OH | $CH_3$ | OH |
| $B_2$ | " | H | OH | H | H | $CH_3$ | OH |
| $B_0$ Serine Analogue | Threonine | H | OH | OH | OH | H | OH |
| $B_5$ Serine Analogue | " | H | OH | OH | H | H | OH |
| $B_1$ | Homotyrosine | H | OH | OH | OH | $CH_3$ | H |
| $D_2$ | *trans* 3-Hydroxyproline, Ornithine | OH | OH | H | H | $CH_3$ | OH |

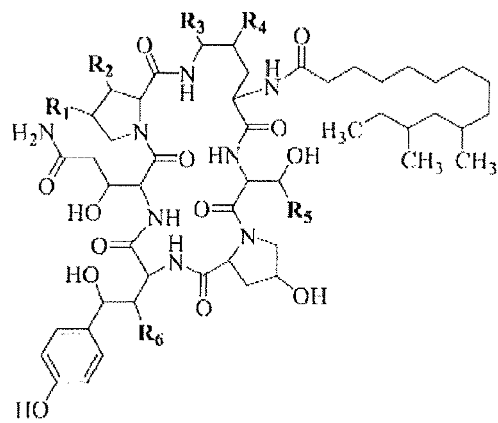

Fig. 2

MUTAGENIZED STRAIN OF *GLAREA LOZOYENSIS* AND A METHOD OF PREPARING A COMPOUND FROM THE MUTAGENIZED STRAIN

FIELD OF THE INVENTION

The present invention relates to the field of antibiotic production. In particular, it relates to a strain producing antibiotic with high yield, the preparation method and use thereof.

BACKGROUND OF THE INVENTION

In the past several decades, both the incidence and the types of fungus infection severely detrimental to human health were continuously increased, especially for the immunosuppressed patients. At the same time, the clinical application of certain commonly used clinical antifungal agents, such as amphotericin, imidazoles and triazoles commonly used clinically, was restricted due to significant neurotoxicity, drug resistance, and the like. Echinocandins, as a kind of novel antifungal agents, are a group of natural products discovered in the 1970s. Structurally, the echinocandins have a similar cyclic polypeptide core but have different fatty acid side chains. Echinocandins can competitively inhibit the synthesis of β-D-glucan in fungal cell walls. The advantages of echinocandins are low toxicity, strong fungicidal activity, and as well as excellent pharmacokinetic properties.

Echinocandins family includes the following member-sechinocandins, cilofungin, pneumocandins, aculeacins, mulundocandin, and WF11899A. Echinocandins and pneumocandins have been actively investigated and are currently applied clinically.

Caspofungin is a water-soluble semi-synthetic derivative of pneumocandin. Merck developed caspofungin as an anti-fungus/pneumocystis agent with a broad spectrum. In a phase II clinical trial with control experiments, it was found that, for the immunosuppressed patients suffering from invasive pulmonary aspergillosis, caspofungin administration (intravenous injection, 50-70 mg/d) achieved good efficacy while administrating amphotericin B and azoles comprising nitrogen did not show any obvious effect. In the 128 cases of HIV infected patients, the efficiency of caspofungin for monilial esophagitis reached 85%, while amphotericin B only had the efficiency of 66.7%. These kinds of drugs can be used to effectively kill fungi which are resistant to azoles comprising nitrogen and amphotericin B. Moreover, these kinds of drugs are superior to traditional antifungal gents, due to the none-hemolytic toxicity and less drug interaction.

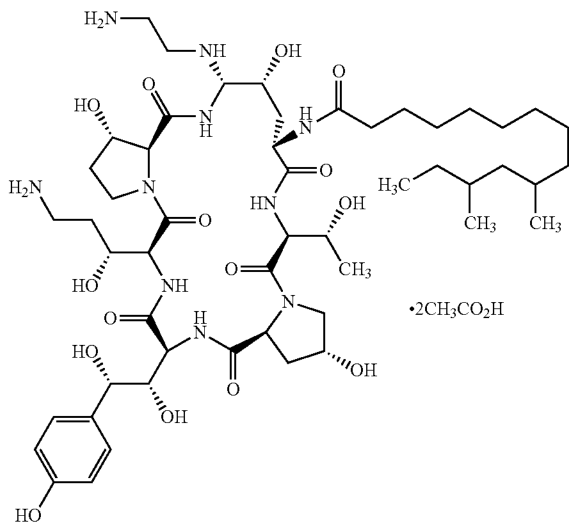 [SMILES: CCC(C)CC(C)CCCCCCCCC(=O)N[C@H]1C[C@@H](O)[C@@H](NCCN)NC(=O)[C@@H]2[C@@H](O)CCN2C(=O)[C@H]([C@H](O)CCN)NC(=O)[C@H]([C@H](O)[C@@H](O)c2ccc(O)cc2)NC(=O)[C@@H]2C[C@@H](O)CN2C(=O)[C@H]([C@@H](C)O)NC1=O]

Structure of Caspofungin

Pneumocandin is a class of natural antifungal drugs produced by *Glarea lozoyensis*. It can be primarily classified into three types according to the different substituents on the proline in its structure: $A_0$ (3-hydroxyl-4-methylproline), $B_0$ (3-hydroxylproline) and $C_0$ (4-hydroxylproline). Moreover, according to the different substituents on the cyclic polypeptides, pneumocandin $A_0$ can be subclassified into six subtypes: $A_0$, $A_1$, $A_2$, $A_3$, $A_4$, and $A_5$; $B_0$ can be subclassified into six subtypes, $B_0$, $B_1$, $B_2$, $B_3$, $B_4$, $B_5$; wherein $A_0$, $A_1$, $A_3$, $A_4$, and $B_0$ are produced by the wild-type strain ATCC20868, with $A_o$ being the major one. Through NMU mutagenesis of ATCC20868, a mutant strain ATCC20957 was obtained which is able to produce $A_0$ and $B_0$ simultaneously. However, ATCC20957 produces $B_0$ with a relatively low capacity, and $A_0$ is produced as an impurity in a relatively high quantity.

Accordingly, it is urgent to find a strain with stable genetic and high-yield properties which can produce more $B_0$ and less $A_0$ for fulfilling the requirements of industrial production.

SUMMARY OF INVENTION

The object of the present invention is to provide a new mutant strain of ATCC20957.

Another object of the present invention is to provide a preparation method of said new strain.

Still another object of the present invention is to provide the use of said new strain.

The fourth object of the present invention is to provide a preparation method to obtain the compound of formula I using said new strain.

In the first aspect of the present invention, a mutagenized strain of *Glarea lozoyensis* is provided, which was deposited in the China General Microbiological Culture Collection Center with the Accession No. CGMCC 2933.

In the second aspect of the present invention, a preparation method of the mutagenized strain mentioned above is provided, comprising the following steps:

(a) mixing a seed liquid of *Glarea lozoyensis* of Accession No. ATCC20957 with nitrosoguanidine to obtain a mixture A;

(b) mixing said mixture A with a wall-breaking enzyme to obtain protoplasts;

(c) regenerating said protoplasts to obtain single colonies;

(d) culturing said single colonies to obtain a mutagenized strain.

In a preferred example, the concentration of the nitrosoguanidine in step (a) is 10-20 μg/ml based on the total volume of said mixture A; and the concentration of the wall-breaking enzyme in step (b) is 10-50 mg/ml based on the total volume upon mixing said mixture A with the wall-breaking enzyme.

In another preferred embodiment, said wall-breaking enzyme comprises one or more of the following: lywallzyme, snail enzyme, and cellulose.

In another preferred embodiment, each enzyme is present at a concentration of 10-40 mg/ml.

In another preferred embodiment, mycelia in the seed liquid in step (a) is in the logarithmic growth phase.

In another preferred embodiment, the dry cell weight is 5-10 g/L based on the total volume of said seed liquid in step (a).

In the third aspect of the present invention, the use of said mutagenized strain for producing the compound of formula I is provided:

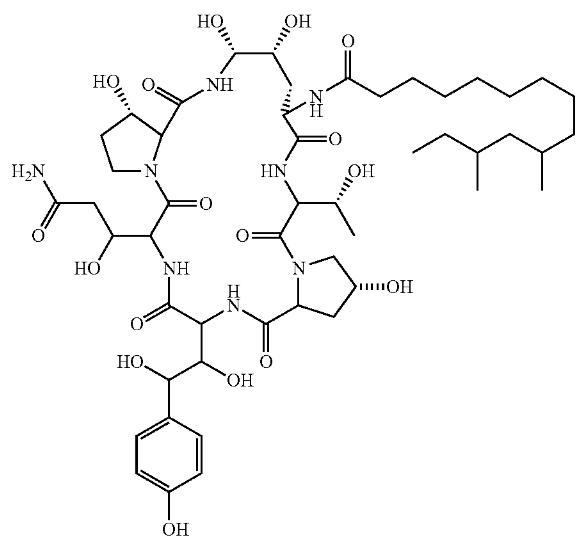

In the fourth aspect of the present invention, a preparation method of the compound of formula I is provided, comprising the following step:

(1) Culturing said mutagenized strain in a fermentation medium at a temperature of 15 to 35□ to obtain the compound of formula I.

In another preferred embodiment, said fermentation medium comprises the following components based on the total volume of the fermentation medium: L-proline 15-50 g/l, sodium glutamate 6-20 g/l, yeast extract 6-20 g/l, fructose 4-20 g/L, inorganic salt 1.5-7 g/L, and trace elements 10-50 g/L.

In another preferred embodiment, said inorganic salt is selected from phosphate or sulfate, or the combination thereof.

In another preferred embodiment, said fermentation medium further comprises 10-100 g/L of mannitol during the culturing.

In another preferred embodiment, the inoculation volume of said mutagenized strain is 4-10 v/v % based on the total volume of the fermentation medium.

In another preferred embodiment, the initial pH value of said fermentation medium is 5.3-6.0.

Summing up, the present invention provides a strain with stable genetic and high-yield properties which can produce more $B_0$ and less $A_0$ for better fulfilling the requirements of industrial production.

DESCRIPTION OF THE DRAWINGS

FIG. 1 shows the flow chart for generating the new strain CGMCC 2933 provided by the present invention.

FIG. 2 shows the structure of Pneumocandins, wherein Pneumocandin $B_0$ is the compound of formula I according to the present invention.

MODES FOR CARRYING OUT THE INVENTION

The present inventors have surprisingly discovered a high-yielding mutant strain (Accession No. CGMCC 2933), which can be obtained by mutagenizing the strain *Glarea lozoyensis* ATCC20957 with nitrosoguanidine (NTG), using lywallzyme to obtain protoplasts, and then screening the regenerated protoplasts. Said mutant strain can produce the compound of formula I with high yield through fermentation. Thus, the inventors accomplished the present invention.

New Strain

The present invention provides a new strain producing the compound of formula I. Taxonomically, said new strain belongs to *Glarea lozoyensis* and has been deposited in the China General Microbiological Culture Collection Center with the Accession No. CGMCC 2933.

Preparation Method of the New Strain

The present invention provides a preparation method of the new strain with Accession No. CGMCC 2933, and said method can be carried out according to the following process:

Starting strain→seed liquid→NTG mutagenesis treatment→removing cell wall by lywallzyme to obtain protoplasts→diluting and plating the protoplasts on dishes→picking single colony and seeding it on the slant→primary screening in shake flasks→selecting high-yielding strain→seeding the strain on the slant→secondary screening in shake flasks→selecting high-yielding strain, verifying in fermentation tank, and performing stability experiment→depositing strain.

In particular, the method provided in the present invention comprises the following steps:

(a) mixing the seed liquid of *Glarea lozoyensis* of Accession No. ATCC20957 with nitrosoguanidine to obtain the mixture A;

(b) mixing said mixture A with the wall-breaking enzyme to obtain protoplasts;

(c) regenerating said protoplasts to obtain single colonies;

(d) culturing said single colonies to obtain new strain.

In an example of the present invention, the new strain can be obtained by the following procedure: culturing ATCC20957 for 1 to 3 days in shake flasks to obtain the seed liquid (dry cell weight, DCW 5-10 g/l), adding an appropriate amount of NTG to the seed liquid, culturing for another 1 to 2 days, and then centrifuging the seed liquid, washing and resuspending the pellet and breaking the cell wall with lywallzyme to obtain protoplasts; diluting the protoplasts, and then plating the diluted protoplasts onto a hypertonic PDA (potato dextrose agar) plate, culturing the protoplasts to obtain recombinant cell single colonies; screening said single colonies to obtain the mutagenized new strain.

Further, the present invention provides a method for producing the compound of formula I by fermenting the new strain obtained by mutagenesis.

In an example of the present invention, the method for obtaining the new strain by mutagenesis and fermenting the new strain to produce the compound of formula I is:

(1) starting strain: *Glarea lozoyensis* ATCC20957

(2) seed culture of the starting strain

The deposited strain ATCC 20957 in glycerol is thawed, seeded in a seed medium (loading amount 50 mL/250 mL), cultured on a shaker at 200-300 rpm at the temperature of 25-30° C. for 1 to 3 days till the dry weight of the mycelia reaches about 5-10 g/L.

The composition of the seed medium is: sucrose 10-20 g/L, yeast extract 4-10 g/L, soybean tryptone 10-20 g/L, $KH_2PO_4$ 1.5-2 g/L, $MgSO_4.7H_2O$ 0.4-1 g/L, trace elements 10-50 g/L, initial pH 5.3-6.0. The medium is sterilized at 121° C. for 20 mins.

Trace elements: $FeSO_4.7H_2O$ 10-20 g/L, $MnSO_4.H_2O$ 10-20 g/L, $ZnSO_4.7H_2O$ 2-10 g/L, $CaCl_2$ 0.7-2.0 g/L, $H_3BO_3$ 0.56-2.0 g/L, $CuCl_2.2H_2O$ 0.25-2.0 g/L, $(NH_4)_6Mo_7O_{24}.7H_2O$ 0.19-2.0 g/L, concentrated hydrochloric acid 500 ml/L.

(3) separation of single colonies

Firstly, the seed liquid of the starting strain is subjected to the treatment of NTG mutagenesis, and then treated by lywallzyme to break cell wall. The resulted protoplast are regenerated to obtain the mutant strain.

(4) screening the mutagenized strain

The protoplasts are plated on a hypertonic PDA medium. The single colonies grown for 10 to 12 days are seeded on a slant medium for further culture, respectively. After 8 to 10 days, the seed medium is inoculated (loading amount 25 mL/250 mL) with the lawn grown on the slant medium, and cultured on a shaker at 280 rpm at the temperature of 25-30° C. for 6 to 10 days. The seed liquid is seeded into the fermentation medium (loading amount 25 mL/250 mL), and cultured on a shaker at 200 to 300 rpm at the temperature of 25-30° C. for 6 to 12 days. After the culture is completed, the fermentation liquid is extracted with methanol, and the content of the compound of formula I in the fermentation liquid is measured by high performance liquid chromatography.

The compositions of the medium involved can be found in Pneumocandins from *Zalerion arboricola*, Journal of antibiotics, Vol 45, No. 12, December 1992, 1867-1874.

Hypertonic PDA plate medium: potato 300 g/L, glucose 20 g/L, agar 15 g/L, sucrose 273.6 g/L, sterilized at 121° C. for 20 mins.

The content of the compound of formula I in the fermentation liquid is measured by high performance liquid chromatography:

chromatographic column Phenomex C18 (4.6 mm×250 mm, 5 μm), mobile phase: acetonitrile water=50:50, column temperature: 35° C., gradient elution, flow rate: 1.0 mL/min, injection volume: 5 μL, detection wavelength: 210 nm.

(5) fermentation of the mutagenized strain

The relevant technical solutions have been reported in literature. For the details, please refer to Biotechnology and Bioengineering, Vol 78, No. 3, May 5, 2002 and Journal of industrial microbiology, 11 (1993), 95-103.

The features of the present invention mentioned above, or the features mentioned in the examples, can be optionally combined. Any feature disclosed in the present specification can be used in combination with any other features, and each feature disclosed in the specification can be replaced with alternative feature which can serve an identical, equivalent, or similar purpose. Therefore, the features disclosed herein are only general exemplary examples of the equivalent or similar features, unless specifically indicated otherwise.

The main advantages of the present invention include:

1. A mutagenized new strain is obtained with stable high-yield and genetic properties.

2. The high genetic stability and low contaminant production of the new strain facilitate the product separation and purification during the production of the compound of formula I as well as the scale-up, thus the new strain being suitable for industrial production.

3. The yield of the compound of formula I can reach 5 g/L under optimized fermentation conditions.

The present invention will be further illustrated below with reference to specific examples. It should be understood that these examples are only to illustrate the present invention but not to limit the scope of the present invention. The experimental methods with no specific conditions described in the following examples are generally performed under conventional conditions or according to the manufacture's instruction. Unless indicated otherwise, all of the percentages, ratios, proportions, or parts are calculated by weight.

The unit of the weight to volume percentage used in the present invention is well known to those skilled in the art, for example, it refers to the weight of solute in a 100 milliliter of solution.

Unless otherwise defined, all the technical and scientific terms used in the present specification have the meanings as commonly understood by those skilled in the art. In addition, all of the methods and materials which are similar or equivalent with the contents disclosed herein can be applied in the present methods. The preferred methods and materials for carrying out the present methods described herein are only given as examples.

In the examples of the present invention, the conditions of the high performance liquid chromatography used to measure the content of the compound of formula I in the fermentation liquid is provided as follows:

chromatographic column: Phenomex C18 (4.6 mm×250 mm, 5 μm), mobile phase: acetonitrile: water=50:50, column temperature: 35° C., gradient elution, flow rate: 1.0 mL/min, injection volume: 5 μL, detection wavelength: 210 nm.

Example 1

Mutagenesis to Obtain the New Strain CGMCC 2933

1. Mutagenesis

The deposited strain ATCC 20957 in glycerol was thawed, seeded in a seed medium with an inoculation amount of 4% (loading amount 50 mL/250 mL), then cultured on a shaker at 280 rpm at 25° C. for 2 days, till the mycelia has a dry weight of about 5-10 g/L. The mutagen NTG was added to the seed liquid at a concentration of 10 μg/mL, and the seed liquid was cultured for another day. And then, 10 mL of the seed liquid containing NTG was taken, centrifuged at 5000 rpm for 10 minutes, and the resulted pellet was washed two times with two volumes of 0.6 M NaCl for removing medium and NTG.

Seed medium: sucrose 10 g/L, yeast extract 5 g/L, soybean tryptone 10 g/L, $KH_2PO_4$ 1.5 g/L, $MgSO_4.7H_2O$ 0.4 g/L, trace elements 10 g/L, initial pH 5.3. The seed medium was sterilized at 121° C. for 20 mins.

Trace elements: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6Mo_7O_{24}.7H_2O$ 0.19 g/L, concentrated hydrochloric acid 500 ml/L.

2. Protoplast Preparation and Single Colony Separation

To the washed mycelia, was added 10 mL of the enzyme mixture (in disodium hydrogen phosphate—citric acid buffer (pH6.0) with 0.5 M NaCl), the enzyme mixture comprising 20 mg/mL of lywallzyme (2000 units/mg), 10 mg/ml of snail enzyme (5 units/mg), and 10 mg/ml of cellulose (15 units/mg). The resultant mixture was shaken at 80 rpm at 30° C. for 5 h for enzymolysis. The enzymolysis reaction mixture was filtered with cotton to remove mycelia and obtain a single-cell suspension comprising only protoplasts. One milliliter of this solution was taken and centrifuged at 14000 rpm for 10 mins. The precipitate was dissolved in 1 mL of disodium hydrogen phosphate—citric acid buffer (pH6.0) comprising 0.5 M NaCl. This solution was then diluted serially into different concentrations, uniformly plated on a hypertonic PDA medium with 0.8 M sucrose, and cultured at 25° C. for 8 to 10 days to obtain single colonies.

3. Screening Process of the High-Yield Strain CGMCC 2933

After culturing for 10 days, single colonies were picked and plated on slant media for further culture. After 8 days, the lawn with an area of 0.5 to 1 $cm^2$ was picked and seeded in a seed medium (loading volume 25 mL/250 mL), cultured on a shaker at 280 rpm and 25° C. for 8 days. The seed liquid was seeded into a fermentation medium at an inoculation volume of 4% (loading volume 25 mL/250 mL), cultured on a shaker at 280 rpm and 25° C. for 14 days (5% mannitol and 0.5% proline were supplemented on day 7 of the culture).

Example 2

Production of the Compound of Formula I by the New Strain CGMCC 2933

The new strain CGMCC 2933 obtained in Example 1 in the seed medium was seeded into a fermentation medium at an inoculation amount of 4%, and cultured in shake flask at the temperature of 25° C. After culturing for 14 days, the yield of the compound of formula I reached 5 g/L (5% mannitol and 0.5% proline were supplemented on day 7 of the culture).

Fermentation medium: L-proline 15 g/L, sodium glutamate 6 g/L, yeast extract (purchased from the Oxiod company) 6 g/L, fructose 4 g/L, $KH_2PO_4$ 1.5 g/L, $MgSO_4.7H_2O$ 0.4 g/L, mannitol 50 g/L, trace elements 10 ml/L, initial pH 5.3. The fermentation medium was sterilized at 121° C. for 20 mins.

Trace elements: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6Mo_7O_{24}.7H_2O$ 0.19 g/L, concentrated hydrochloric acid 500 ml/L.

COMPARATIVE EXAMPLE

The capacity of the starting strain ATCC 20957 for producing the compound of formula I was compared with that of the mutant strain CGMCC 2933 using the following methods:

The starting strain and the mutant strain were cultured using the culture method described in Example 2, respectively. After the culture was completed, the fermentation liquid was extracted using two volumes of methanol, and content of the compound of formula I in the fermentation liquid was measured with high performance liquid chromatography. The results are shown in Table 1.

TABLE 1

| Strain No. | Yield of the compound of formula I ($g \cdot L^{-1}$) |
|---|---|
| ATCC20957 | 1.1 |
| CGMCC 2933 | 5.2 |

The media used are listed as follows:

Screening medium: potato 300 g/L, glucose 20 g/L, agar 15 g/L, sucrose 273.6 g/L, sterilized at 121° C. for 20 mins.

Slant medium: potato 300 g/L, glucose 20 g/L, agar 15 g/L, sterilized at 121° C. for 20 mins.

Seed medium: sucrose 10 g/L, yeast extract 5 g/L, soybean tryptone 10 g/L, $KH_2PO_4$ 1.5 g/L, $MgSO_4.7H_2O$ 0.4 g/L, trace elements 10 g/L, initial pH 5.3, sterilized at 121° C. for 20 mins.

Fermentation medium: L-proline 15 g/L, sodium glutamate 6 g/L, yeast extract (purchased from the Oxiod company) 6 g/L, fructose 4 g/L, $KH_2PO_4$ 1.5 g/L, $MgSO_4.7H_2O$ 0.4 g/L, mannitol 50 g/L, trace elements 10 ml/L, initial pH 5.3, sterilized at 121° C. for 20 mins.

Trace elements: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6MO_7O_{24}.7H_2O$ 0.19 g/L, concentrated hydrochloric acid 500 ml/L.

Example 3

Stability of the New Strain CGMCC 2933

Subculture was carried out using the same medium and culture conditions described in Example 2. The result is shown in Table 3.

TABLE 3

Passage stability of the new strain

| Passage number | F1 | F2 | F6 |
|---|---|---|---|
| Yield of the compound of formula I (g/L) | 5.2 | 5.0 | 5.3 |

The result shows that the new strain has an excellent stability.

The above description is merely the preferred examples of the present invention, and is not intended to limit the scope of the substantial technical contents of the present invention. The substantial technical contents of the present invention are broadly defined in the scope of the claims appended to the present application. Any technical entity or method accomplished by others should be deemed as falling into the scope of the claims of the present application if the entity or method is completely identical with that defined in the claims of the present application or an equivalent change or modification thereof.

The invention claimed is:

1. A mutagenized strain of *Glarea lozoyensis*, deposited in China General Microbiological Culture Collection Center with the Accession No, CGMCC 2933.

2. The mutagenized strain of claim 1, wherein the strain produces the compound shown in formula I:

I

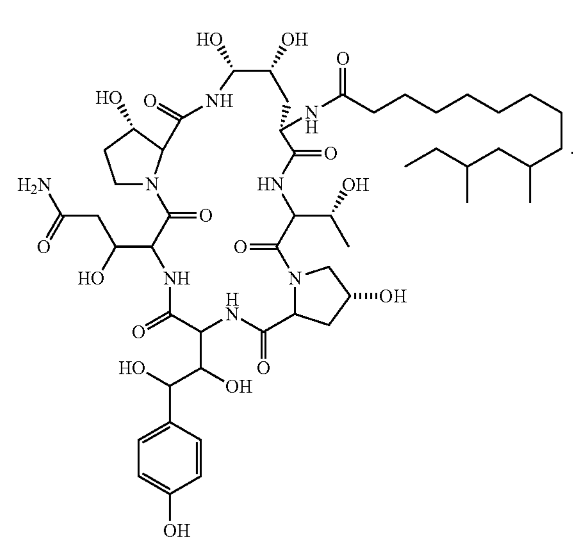

3. A method of making a compound of the following formula I:

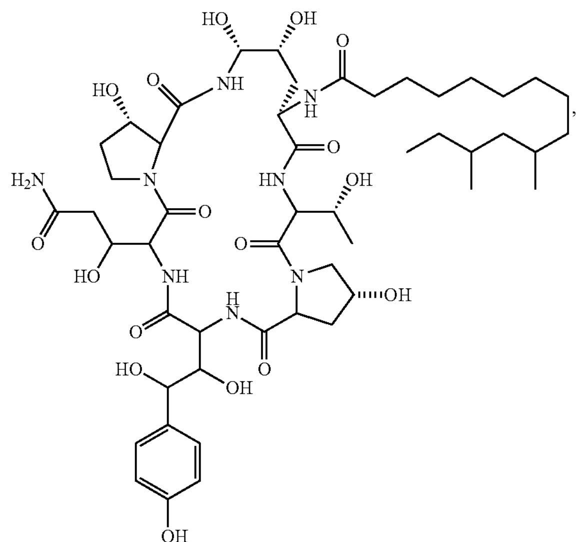

wherein said method comprises the following step:

culturing said mutagenized strain of claim 1 in a fermentation medium at a temperature of 15 to 35° C. and isolating the compound of formula I from the culture, the fermentation medium comprising the following components based on the total volume of the fermentation medium: L-proline 15 g/l, sodium glutamate 6 g/l, yeast extract 6 g/l, fructose 4 g/l, inorganic salt 1.5 g/l, and trace elements 10 ml/l.

4. The preparation method of claim 3, wherein said inorganic salt is selected from phosphate or sulfate, or the combination thereof.

5. The preparation method of claim 3, wherein said fermentation medium further comprises 10-100 g/L of mannitol during the culturing.

6. The preparation method of claim 3, wherein an inoculation volume of said mutagenized strain is 4-10 v/v % based on the total volume of the fermentation medium.

7. The preparation method of claim 3, wherein an initial pH value of said fermentation medium is 5.3-6.0.

8. The preparation method of claim 3, wherein the trace elements include the following: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6Mo_7O_{24}.7H_2O$ 0.19 g/L, and concentrated hydrochloric acid 500 ml/L.

* * * * *